United States Patent
Nair et al.

(10) Patent No.: US 9,092,552 B2
(45) Date of Patent: Jul. 28, 2015

(54) SYSTEM MONITOR FOR MONITORING FUNCTIONAL MODULES OF A SYSTEM

(71) Applicant: CYBERONICS, INC., Houston, TX (US)

(72) Inventors: Sujith V. Nair, Houston, TX (US); Jamin L. Gingerich, Gilbert, AZ (US); Tushar R. Desai, Pearland, TX (US); Brian C. Tomayko, Webster, TX (US)

(73) Assignee: CYBERONICS, INC., Houston, TX (US)

( * ) Notice: Subject to any disclaimer, the term of this patent is extended or adjusted under 35 U.S.C. 154(b) by 165 days.

(21) Appl. No.: 13/872,020

(22) Filed: Apr. 26, 2013

(65) Prior Publication Data

US 2014/0325287 A1  Oct. 30, 2014

(51) Int. Cl.
| | |
|---|---|
| *G06F 11/00* | (2006.01) |
| *G06F 11/34* | (2006.01) |
| *G06F 11/07* | (2006.01) |
| *G06F 11/30* | (2006.01) |
| *A61B 5/1495* | (2006.01) |

(52) U.S. Cl.
CPC ............. *G06F 11/34* (2013.01); *A61B 5/1495* (2013.01); *G06F 11/0757* (2013.01); *G06F 11/0796* (2013.01); *G06F 11/3013* (2013.01); *G06F 11/0793* (2013.01)

(58) Field of Classification Search
None
See application file for complete search history.

(56) References Cited

U.S. PATENT DOCUMENTS

| | | | |
|---|---|---|---|
| 3,898,984 A | 8/1975 | Mandel et al. | |
| 4,809,697 A | 3/1989 | Causey, III et al. | |
| 4,839,806 A | 6/1989 | Goldfischer et al. | |
| 5,014,190 A | 5/1991 | Johnson | |
| 5,321,618 A | 6/1994 | Gessman | |
| 5,607,458 A * | 3/1997 | Causey et al. | 607/27 |
| 5,669,391 A | 9/1997 | Williams | |
| 5,683,430 A | 11/1997 | Markowitz et al. | |
| 5,709,216 A | 1/1998 | Woodson, III | |
| 5,720,771 A | 2/1998 | Snell | |
| 5,802,271 A * | 9/1998 | Hashimoto et al. | 714/44 |
| 5,814,088 A | 9/1998 | Paul et al. | |
| 5,833,623 A | 11/1998 | Mann et al. | |
| 5,891,179 A | 4/1999 | Er et al. | |
| 5,897,577 A | 4/1999 | Cinbus et al. | |
| 6,317,633 B1 | 11/2001 | Jorgenson et al. | |
| 6,360,333 B1 * | 3/2002 | Jansen et al. | 714/25 |
| 6,442,432 B2 | 8/2002 | Lee | |
| 6,490,486 B1 | 12/2002 | Bradley | |
| 6,497,655 B1 | 12/2002 | Linberg et al. | |
| 6,569,094 B2 | 5/2003 | Suzuki et al. | |
| 6,584,587 B1 * | 6/2003 | McDermott | 714/55 |
| 6,687,538 B1 | 2/2004 | Hrdlicka et al. | |

(Continued)

FOREIGN PATENT DOCUMENTS

EP    1139861    12/1999

*Primary Examiner* — Gabriel Chu
(74) *Attorney, Agent, or Firm* — Cyberonics, Inc.

(57) ABSTRACT

A method includes detecting a counter event at a system monitor of a system. The method also includes, in response to detecting the counter event, checking a state of each flag of a first set of flags. Each of the first set of flags is associated with a monitored module of the system, and the state of each of the first set of flags is indicated by a value at a memory location that is enabled. The method also includes, in response to determining that at least one flag of the first set of flags has a value indicating an error associated with a particular monitored module, causing an action to be performed at the system.

20 Claims, 6 Drawing Sheets

(56) References Cited

U.S. PATENT DOCUMENTS

| | | | |
|---|---|---|---|
| 6,718,486 B1 * | 4/2004 | Roselli et al. | 714/41 |
| 6,721,600 B2 | 4/2004 | Jorgenson et al. | |
| 6,878,112 B2 | 4/2005 | Linberg et al. | |
| 6,957,107 B2 | 10/2005 | Rogers | |
| 7,130,695 B2 | 10/2006 | Czygan et al. | |
| 7,218,967 B2 | 5/2007 | Bergelson et al. | |
| 7,280,867 B2 | 10/2007 | Frei et al. | |
| 7,295,881 B2 | 11/2007 | Cohen | |
| 7,356,740 B2 | 4/2008 | Neumiller et al. | |
| 7,389,144 B1 | 6/2008 | Osorio | |
| 7,676,263 B2 | 3/2010 | Harris et al. | |
| 7,717,112 B2 | 5/2010 | Sun et al. | |
| 8,056,120 B2 | 11/2011 | Kusakari | |
| 2003/0135781 A1 * | 7/2003 | Da Palma et al. | 714/2 |
| 2003/0158700 A1 | 8/2003 | Forler et al. | |
| 2004/0138724 A1 * | 7/2004 | Sieracki et al. | 607/60 |
| 2005/0038326 A1 | 2/2005 | Mathur | |
| 2005/0246580 A1 * | 11/2005 | Fairhurst et al. | 714/11 |
| 2005/0278518 A1 | 12/2005 | Ko et al. | |
| 2006/0203740 A1 * | 9/2006 | Chang et al. | 370/252 |
| 2007/0055164 A1 | 3/2007 | Huang et al. | |
| 2008/0140161 A1 * | 6/2008 | Goetz et al. | 607/60 |
| 2008/0221644 A1 | 9/2008 | Vallapureddy et al. | |
| 2010/0088539 A1 * | 4/2010 | Stubbs et al. | 714/3 |
| 2010/0162054 A1 | 6/2010 | Asuncion et al. | |
| 2011/0208009 A1 | 8/2011 | Fu et al. | |
| 2011/0213877 A1 | 9/2011 | Plummer et al. | |

* cited by examiner

SYSTEM MONITOR FOR MONITORING FUNCTIONAL MODULES OF A SYSTEM

FIELD OF THE DISCLOSURE

The present disclosure is generally related to monitoring systems and implantable medical devices.

BACKGROUND

Over the years there has been increasing use of computer systems generally and growth in use of embedded systems. Embedded systems include systems that may be difficult to troubleshoot, including systems that are unreachable, such as implanted medical devices or remotely controlled devices. Many types of embedded systems use monitoring systems to monitor system elements. Monitoring systems may be relatively complex to design, build, and maintain and may be relatively resource-intensive, especially for real-time or embedded systems. Additionally, some monitoring systems are relatively inflexible. For example, such a monitoring system may monitor a limited numbers of events, may have limited response capabilities to detected events available, and may be difficult to reconfigure.

SUMMARY

Embodiments disclosed herein include a system monitor to monitor one or more functional modules of a monitored device, such as an implantable medical device. The system monitor includes a timer or a counter that counts off a monitoring period. Each monitored functional module is associated with a flag (e.g., a memory location that stores a particular value). A first value of the flag may indicate normal operation of the monitored functional module, and a second value of the flag may indicate an error condition at the monitored functional module.

When a particular functional module is operating normally, the particular functional module sets the value of the flag associated with the particular function module to the first value (indicating normal operation) during a monitoring period. Conversely, if the particular functional module is not operating normally (e.g., has experienced a fault or failure), the particular functional module does not set the value of the flag associated with the particular function module to the first value during a monitoring period.

Upon expiration of the monitoring period, the system monitor checks the flags associated with monitored functional modules. If any of the monitored functional modules (e.g., the particular functional module) has failed to reset the value at its corresponding flag to the first value, the flag will have the second value (indicating a failure). Thus, the system monitor can detect functional modules that had errors during the monitoring period. The system monitor may then reset values at the flags and start another monitoring period. At the end of each expiration period, if the system monitor detects that a flag has not been set to the first value, the system monitor may initiate an action associated with that flag.

In a particular embodiment, to provide increased flexibility of the system monitor, a register (or other memory location) or a set of registers may be dynamically associated with (e.g., assigned to store a value of a flag associated with) a particular functional module. In this embodiment, the particular functional module may provide an enable signal to the register that is assigned to store the flag associated with the particular functional module. Thus, the system monitor may check flags only at enabled registers (e.g., registers that have received or are receiving an enable signal from a functional module). Further, flags may be assigned to hardware memory locations using configurable software, which may simplify design of the monitoring system. Additionally, different monitoring periods may be used for monitoring different functional modules.

In a particular embodiment, a method includes detecting a counter event at a system monitor of a system. The method also includes, in response to detecting the counter event, checking a state of each flag of a first set of flags. Each of the first set of flags is associated with a monitored module of the system, and the state of each of the first set of flags is indicated by a value at a memory location that is enabled. The method also includes, in response to determining that at least one flag of the first set of flags has a value indicating an error associated with a particular monitored module, causing an action to be performed at the system.

In a particular embodiment, a system may include circuitry configured to detect a counter event at a system monitor. The system also includes circuitry configured to, in response to detecting the counter event, check a state of each flag of a first set of flags. Each of the first set of flags is associated with a monitored module of the system, and the state of each of the first set of flags is indicated by a value at a memory location that is enabled. The system also includes circuitry configured to, in response to determining that at least one flag of the first set of flags has a value indicating an error associated with a particular monitored module, cause an action to be performed at the system.

A particular embodiment includes a computer-readable storage device that stores instructions that are executable by a processor to cause the processor to perform operations including detecting a counter event at a system monitor. The operations also include, in response to detecting the counter event, checking a state of each flag of a first set of flags. Each of the first set of flags is associated with a monitored module of a system, and the state of each of the first set of flags is indicated by a value at a memory location that is enabled. The operations further include, in response to determining that at least one flag of the first set of flags has a value indicating an error associated with a particular monitored module, causing an action to be performed at the system.

DETAILED DESCRIPTION

Figure 1:
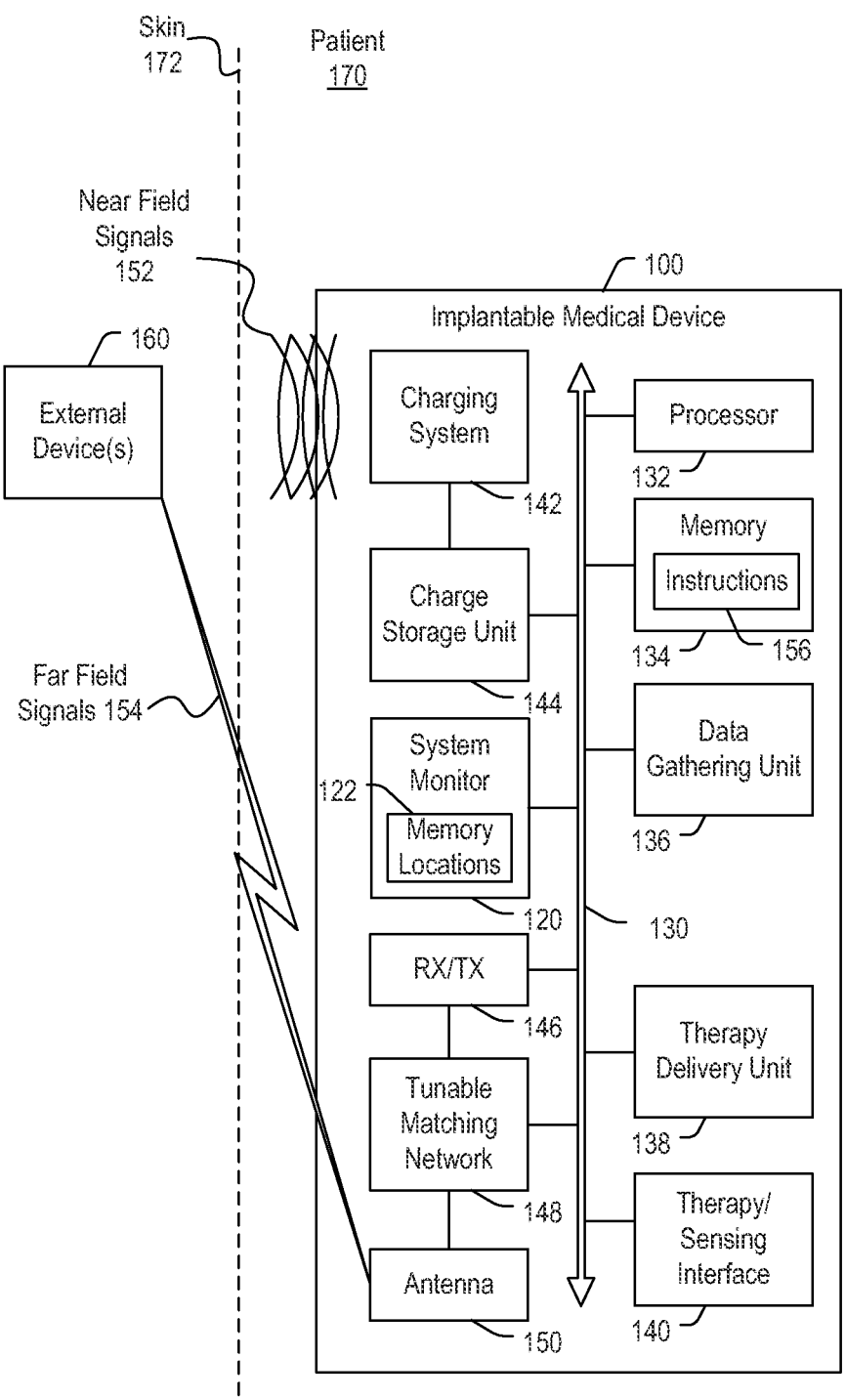
FIG. 1 is a block diagram of a particular embodiment of a system including an implantable medical device.

FIG. 1 illustrates a particular embodiment of a system including an implantable medical device (IMD) 100. The IMD 100 may include a cardiac pacemaker, a nerve stimulation device, an implantable drug delivery device, a body parameter sensing device, a device to implement other therapy or sensing functions internal to the patient's body, or combinations thereof. During use, the IMD 100 may be implanted within a patient 170 (e.g., beneath skin 172 of the patient 170). The system of FIG. 1 also includes an external device or devices 160. The external device(s) 160 may be positioned external to the patient 170 and may interact with the IMD 100 (e.g., using near field signals 152, far field signals 154, or both).

The IMD 100 may include multiple components, which are also referred to herein as modules. Each module may include circuitry, electrical or electromechanical components, software executable by a processor 132, or combinations thereof. The IMD 100 may also include the processor 132 and memory 134 accessible to the processor 132. The memory 134 may store instructions 156 that are executable by the processor 132 to control the IMD 100 or one or more modules of the IMD 100. The processor 132 may be a digital signal processor (DSP), a microcontroller, or another device capable of executing instructions from the memory 134. The modules of the IMD 100 may include the processor 132, the memory 134, a data gathering unit 136, a therapy delivery unit 138, a therapy/sensing interface 140, a charging system 142, a charge storage unit 144, a system monitor 120, a transceiver (RX/TX) 146, a tunable matching network 148, an antenna 150, a communication bus 130, other functional modules, or a combination thereof. In a particular embodiment, the system monitor 120 is configured to monitor one or more of the modules of the IMD 100, as described further below.

The transceiver 146, the tunable matching network 148, and the antenna 150 together may be referred to as communication circuitry. The communication circuitry may facilitate communication between the IMD 100 and the external device(s) 160 using the far field signals 154. For example, the IMD 100 may use the far field signals 154 to receive programming information, such as instructions or operating parameters to be stored at the memory 134. In this example, the external device(s) 160 may include a programming device, and the processor 132 may control the therapy delivery unit 138, the data gathering unit 136, the therapy/sensing interface 140, or a combination thereof, based on the programming information received from the programming device.

Alternatively or in addition, the IMD 100 may use the far field signals 154 to send sensed data gathered by the data gathering unit 136 to the external device(s) 160. For example, the data gathering unit 136 may gather body parameter data, such as temperature, blood pressure, blood oxygen saturation, heart rate, electromyography data, electroencephalograph data, electrocardiogram data, other body parameter data, or a combination thereof. In a particular embodiment, the body parameter data gathered by the data gathering unit 136 may be used by the processor 132 to control therapy delivered by the therapy delivery unit 138. Alternatively or in addition, the body parameter data may be stored, or processed and stored, at the memory 134.

The therapy delivery unit 138 may provide a therapy or treatment to the patient 170. For example, the therapy delivery unit 138 may include a drug pump configured to deliver a drug to the patient, an electrostimulation device configured to deliver electrical stimulation to tissue of the patient 170, another stimulation, therapy or treatment device, or a combination thereof. The therapy delivery unit 138 may operate in an open-loop mode or a closed-loop mode. In the open-loop mode, therapy delivered by the therapy delivery unit 138 may be pre-programmed (e.g., without feedback based on the delivered therapy, without feedback based on sensed body parameter data, or without both). In the closed-loop mode, the therapy delivery unit 138 may provide therapy responsive to feedback based on gathered body parameter data.

The therapy/sensing interface 140 enables the IMD 100 to couple to one or more electrodes or sensors (not shown). For example, the therapy/sensing interface 140 may couple the IMD 100 to one or more electrodes that interface to the patient's body to generate and/or control electrical impulses. In another example, the therapy/sensing interface 140 may couple sensors or electrodes to sense physiological parameters, such as action potentials in a nerve or other body parameters.

In a particular embodiment, the system monitor 120 may be embedded within or coupled to another module of the IMD 100. For example, the system monitor 120 may be a component of or embedded within the processor 132. The system monitor 120 may monitor one or more functional modules of the IMD 100 and may initiate one or more actions to be carried out as a result of detecting an event at one or more of the monitored modules. For example, if the system monitor 120 detects an event that indicates an error at the processor 132, the memory 134, the data gathering unit 136, the therapy delivery unit 138, the therapy/sensing interface 140, the charging system 142, the charge storage unit 144, the system monitor 120, the transceiver (RX/TX) 146, the tunable matching network 148, the antenna 150, the communication bus 130, other functional modules, or a combination thereof, the system monitor 120 may initiate a responsive action.

In a particular embodiment, the system monitor 120 includes or has access to a plurality of memory locations 122. Although the memory locations 122 are illustrated in FIG. 1 as being part of the system monitor 120, in other embodiments, the memory locations 122 may be separate from the system monitor 120. For example, the memory locations 122 may be part of the memory 134. In other embodiments, the memory locations 122 are dedicated registers within the system monitor 120 or within other circuitry of the IMD 100. One or more of the memory locations 122 may be associated with a corresponding monitored module. For example, a module of the IMD 100 that is associated with a particular memory location may provide an enable signal to the memory location (e.g., to enable a particular register).

During a monitoring period, a monitored module corresponding to a particular memory location may provide the enable signal to the memory location and may set a value at the particular memory location. At an expiration of the monitoring period, the system monitor 120 may determine whether each of the memory locations 122 (or each enabled memory location) has a first value (e.g., a one (1)) indicating that the corresponding monitored module is functioning properly. If each of the memory locations 122 (or each enabled memory location) has the first value indicating that the corresponding monitored module is functioning properly, the system monitor 120 may reset the values at the memory locations 122 to a second value (e.g., zero (0)) and may start a new monitoring period (e.g., reset a timer or counter). The second value may indicate an error condition. Thus, when a monitored module fails to store the first value at its corresponding memory location during the monitoring period, the corresponding memory location may store the second value at the expiration of the monitoring period, indicating an error condition at the monitored module.

In a particular embodiment, the system monitor 120 initiates a responsive action when an event (e.g., an error condition) is associated with a monitored module. The system monitor 120 may select the responsive action based on values stored at the plurality of memory locations. For example, by examining the values stored at the plurality of memory locations, the system monitor 120 may determine which monitored module or modules are associated with error conditions.

The system monitor 120 may select a particular responsive action based on which monitored module or modules are associated with error conditions. In another embodiment, the system monitor 120 may initiate a particular action (such as a patient safety action) regardless of which monitored module or modules are associated with error conditions. For example, the system monitor 120 may disable application of therapy to the patient when any monitored module (including a module distinct from the therapy delivery unit 138) is associated with an error condition. In this embodiment, patient safety is maintained regardless of which monitored module experiences an error condition.

In a particular embodiment, multiple responsive actions may be initiated. For example, when any monitored module is associated with an error condition, the system monitor 120 may disable application of therapy to the patient. Additionally, the system monitor 120 may initiate a reset action (e.g., by providing a reset signal) associated with the monitored module that is associated with the error condition, or may initiate a reset of one or more other components of the IMD 100 (e.g., a system-wide reset of the IMD 100 or a reset of the processor 132). After the reset, the IMD 100 may remain in a state in which therapy delivery to the patient is disabled for one or more monitoring periods (e.g., until one or more monitoring periods occur with no detected error). Alternately, the reset may cause therapy delivery to the patient to be re-enabled. Therapy delivery to the patient may be disabled by disabling application of power to the therapy delivery unit 138, by modifying operating parameters associated with the therapy delivery unit 138 (e.g., at the processor 132 or the memory 134), by providing an instruction to the processor 132 to disable the therapy delivery unit 138, by disabling a clock signal provided to the processor 132 or to the therapy delivery unit 138, by actuating a switch (not shown) between the charge storage unit 144 and the therapy delivery unit 138 or between the therapy delivery unit 138 and the therapy/sensing interface 140, by actuating a switch of the therapy/sensing interface 140 to disconnect the therapy delivery unit 138 from electrodes coupled to the patient 170, by other mechanisms that prevent the therapy delivery unit 138 from providing therapy to the patient, or a combination thereof.

The system monitor 120 may also store data associated with detected error conditions at the memory 134. After an error condition is detected by the system monitor 120 and after particular functions of the IMD 100 are disabled by the system monitor 120, the IMD 100 may be reset based on an input received from the external device(s) 160. For example, the IMD 100 may transmit data related to a detected error condition to the external device(s) 160. The patient 170 or a health care provider may review data and initiate or perform one or more corrective actions. Afterwards, the patient 170 or the health care provider may send a signal from the external device(s) 160 to the IMD 100 that causes therapy delivery to the patient 170 to be reactivated.

Accordingly, the system monitor 120 may enable flexible and dynamic configuration of monitoring of the modules or components of the IMD 100. For example, since each of the modules may provide an enable signal to a corresponding memory location to generate an enabled flag, each module can dynamically and independently of other modules, opt into or opt out of monitoring.

Figure 2:
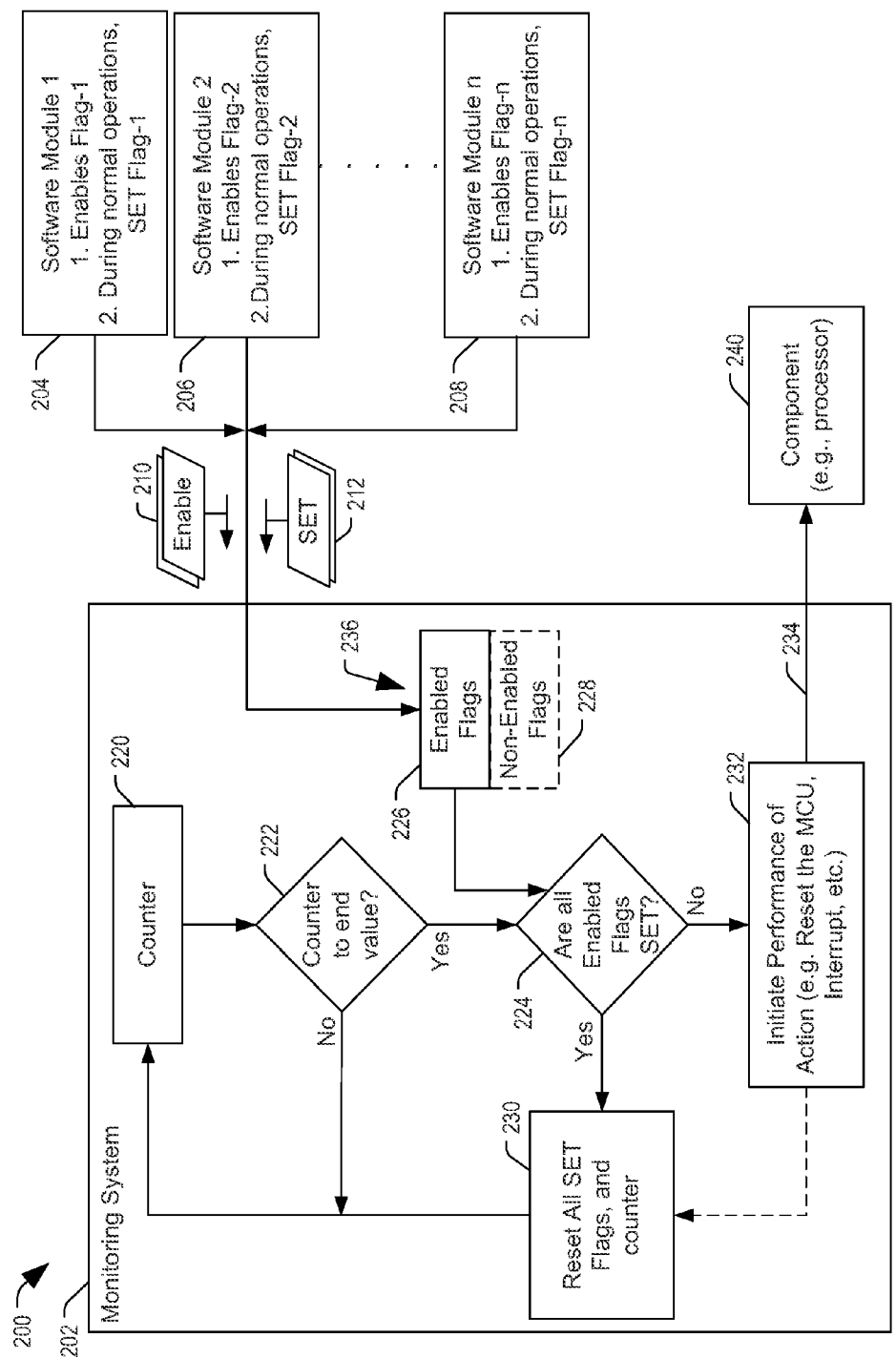
FIG. 2 is a functional block diagram a particular embodiment of a monitoring system.

FIG. 2 is a functional block diagram of a particular embodiment of a monitoring system 202. In FIG. 2, the monitoring system 202 includes or has access to one or more memory locations 236 (e.g., registers corresponding to flags) and a counter 220. The memory locations 236 may include, but are not limited to, one or more dedicated registers, one or more general purpose registers, or a generally addressable memory that is allocated for use as a register. In a particular embodiment, the monitoring system 202 includes, is included within, or corresponds to the system monitor 120 of FIG. 1.

The memory locations 236 store one or more flags (e.g., stored logical values that each have a SET state or a NOT SET state), which may each include one or more bits. Each memory location may be enabled by and settable (e.g., writable) by a functional module of an implantable medical device, such as the IMD 100 of FIG. 1. When a memory location is enabled, it may be referred to as an enabled flag, such as one or more enabled flags 226. When the memory location is not enabled, it may be referred to as a non-enabled flag, such as one or more non-enabled flags 228. In FIG. 2, the monitoring system 202 monitors one or more functional modules, such as a first software module 204, a second software module 206, and an nth software module 208. The functional modules may include, may be included within, or may correspond to the functional modules of the IMD 100 of FIG. 1, such as the processor 132, the memory 134, the data gathering unit 136, the therapy delivery unit 138, the therapy/sensing interface 140, the charging system 142, the charge storage unit 144, the system monitor 120, the transceiver (RX/TX) 146, the tunable matching network 148, the antenna 150, the communication bus 130, or a combination thereof The counter 220 may include a timer or another device that monitors (e.g., counts) time or clock cycles. The monitoring system 202 may use the counter 220 to determine when a monitoring period ends. For example, at the beginning of each monitoring period, the monitoring system 202 may set the counter 220 to a starting value (e.g., an initial value). The counter 220 may then count down (e.g., decrement) from the starting value to an ending value (e.g., zero (0) or another value that is less than the starting value). When the counter 220 reaches the ending value, at 222, the monitoring system 202 may determine that a monitoring period has ended and may check, at 224, a value at each of the enabled flags 226. In another example, the counter 220 may count up from the starting value to the ending value. Regardless of whether the counter 220 counts down or counts up, when the counter 220 reaches the ending value, the monitoring system 202 may determine that a monitoring period has ended and may check a value at each of the enabled flags 226. For simplicity of the description, the counter 220 is described herein as counting down from a designated starting value to an ending value of zero (0).

At a beginning of a first monitoring period, the monitoring system 202 resets the counter 220 to the starting value. Each software module 204, 206 and 208 executes according to its particular program of instructions. At least one instruction of each software module 204, 206, 208 is executable to cause an enable signal 210 to be provided to a memory location 236 of the monitoring system 202. For example, the first software module 204 may include an instruction that, when executed, causes an enable signal to be provided to a first memory location, the second software module 206 may include an instruction that, when executed, causes an enable signal to be provided to a second memory location, and the nth software module 208 may include an instruction that, when executed, causes an enable signal to be provided to an nth memory location. Alternatively, instructions that are distinct from the software modules 204, 206, 208 may cause the enable signals 210 to be provided to the memory locations 236 based on a set of software modules that are to be monitored. For example, instructions associated with the monitoring system 202 or configuration instructions associated with a device that includes the monitoring system 202 (such as the IMD 100)

may cause the enable signals 210 to be provided to the memory locations 236 based on the software modules 204, 206, 208 that are to be monitored.

At least one instruction of each software module 204, 206, 208 may be executable to cause a SET flag command 212 to be sent to an enabled flag (e.g., a memory location associated with an enable signal) corresponding to the software module. For example, the first software module 204 may include an instruction that, when executed, causes a flag at the first memory location to be set, the second software module 206 may include an instruction that, when executed, causes a flag at the second memory location to be set, and the nth software module 208 may include an instruction that, when executed, causes a flag at the nth memory location to be set. As used herein, setting a flag refers to storing a value indicating a "SET" condition at a particular memory location. For example, each memory location may store a single bit, such as a logical 0 or a logical 1. In this example, when the memory location stores a logical 0, the flag may be considered not SET. Conversely, when the memory location stores a logical 1, the flag may be considered SET. Thus, in this example, the SET flag command 212 indicates that a logical 1 value is stored at the memory location. In various embodiments, other logical values besides or in addition to logical 0 and logical 1 may be used. Further, more than one bit may be used for each flag. Moreover, meaning assigned to each value may be changed. To illustrate, a logical 0 value may indicate that a flag is SET, and a logical 1 value may indicate that the flag is not SET.

During each monitoring period, each of the software modules 204, 206, 208 may set its corresponding flag if the software module is operating properly. For example, when the first software module 204 executes during a first monitoring period, the first software module 204 may set the flag at the first memory location (e.g., responsive to an instruction of the first software module 204). Upon expiration of each monitoring period (e.g., when the counter 220 reaches the ending value), the monitoring system 202 checks values stored at each enabled flag, at 224. Since the software modules 204, 206, 208 provide the enable signals 210, the monitoring system 202 is able to determine which flags among the set of memory locations 236 should be SET. For example, in the embodiment of FIG. 2, each enabled flag 226 should be set by a respective software module during each monitoring period. Accordingly, the monitoring system 202 does not require extensive configuration in order to monitor new software modules. Additionally, if a software module is modified, the software module does not require extensive configuration to report proper functioning to the monitoring system 202. Rather, the monitoring system 202 can monitor a software module merely by providing one or more instructions (e.g., in the software module) that point to an assigned memory location and that cause the software module to provide an enable signal 210 to the assigned memory location when the software module is to be checked by the monitoring system 202 and to provide a SET flag command 212 to the assigned memory location when the software module is functioning properly.

In a particular embodiment, the software modules 204, 206, 208 may have different execution times and therefore may be monitored at different time intervals. In this embodiment, one or more of the software modules 204, 206, 208 may provide the enable signal 210 less frequently than once per monitoring period. For example, the first software module 204 may have a different execution time than another software module, such as the second software module 206. In this example, the first software module 204 and the second software module 206 may provide enable signals 210 at different rates. To illustrate, the first software module 204 may provide an enable signal every 20 ms, and the second software module 206 may provide an enable signal every 50 ms. If the counter 220 counts off monitoring periods of 20 ms, then the memory location assigned to the first software module 204 should be enabled every monitoring period. Accordingly, at the end of each monitoring period, the monitoring system 202 will check the enabled flag at the memory location assigned to the first software module 204 to determine whether the first software module 204 is functioning properly. However, the memory location assigned to the second software module 206 should be enabled approximately every third monitoring period. Accordingly, at the end of every third monitoring period, the monitoring system 202 will check the enabled flag at the memory location assigned to the second software module 206 to determine whether the second software module 206 is functioning properly.

If any of the enabled flags are not SET, at 224, the monitoring system 202 may initiate performance of a particular action, at 232. For example, the monitoring system 202 may send a command 234 to another component 240 (such as a processor). The particular action performed (or the particular command 234 sent) may depend on which enabled flag was not SET. An example of an action that may be performed includes resetting or rebooting the system 200 or the component of the system 200. Another example of an action that may be performed includes turning off a feature, function or component of the system 200. To illustrate, when the system 200 includes or corresponds to the IMD 100, the data gathering unit 136, the therapy delivery unit 138, the therapy/sensing interface 140, or the transceiver 146 may be turned off or disabled (e.g., as a patient safety measure).

If no enabled flag is not SET, at 224, the monitoring system 202 may reset each SET flag and the counter 220, at 230. Thus, a subsequent monitoring period may begin. In some embodiments, after the monitoring system 202 sends the command 234, the monitoring system 202 may also reset each SET flag and the counter 220, at 230.

Accordingly, the system of FIG. 2 may enable flexible and dynamic configuration of the monitoring system 202. For example, different monitored modules, such as the software modules 204, 206, 208, may be assigned to different memory locations. Since each monitored module may provide an enable signal to the corresponding memory location to generate an enabled flag, each module can dynamically and independently of other modules, opt into or opt out of monitoring.

Figure 3:
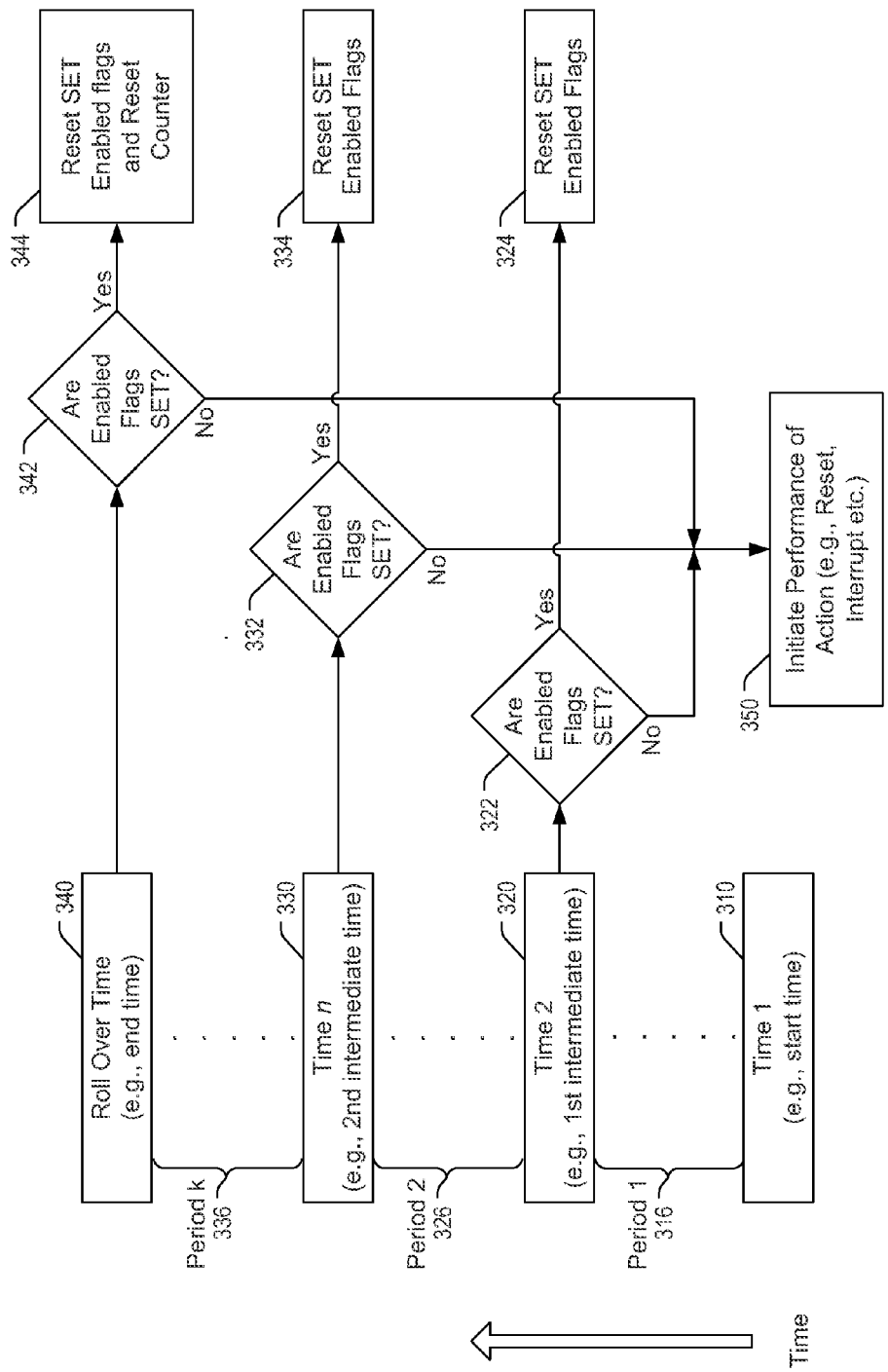
FIG. 3 is a diagram illustrating an embodiment of a method that may be implemented by a system monitor.

FIG. 3 is a diagram illustrating another embodiment of a method that may be implemented by a system monitor, such as the system monitor 120 of FIG. 1 or the monitoring system 202 of FIG. 2. The embodiment illustrated in FIG. 3 relates to using a counter (such as the counter 220) to count from a start time (e.g., a first time 310) to an end time (e.g., a roll over time 340) and checking enabled flags at the end time as well as at one or more intermediate times (such as a second time 320 and an nth time 330) between the start time and the end time.

In the diagram of FIG. 3, time proceeds from bottom to top, i.e., from the first time 310 to the roll over time 340. During operation, the counter may count from the first time 310 to the second time 320 (e.g., a first intermediate time between the start time and the end time). When the second time 320 is reached, the monitoring system may determine, at 322, whether enabled flags of a memory location are SET. When the enabled flags are SET, the monitoring system may reset the enabled flags, at 324. When one or more of the enabled flags is not SET, the monitoring system may initiate performance of an action, at 350. Examples of actions that may be initiated include, but are not limited to, resetting or interrupting of a processor, generating a notification message, disabling one or more other components of a device (such as an implantable medical device), or a combination thereof. To illustrate, when the monitored device is the IMD 100 of FIG. 1, the responsive action may include resetting, interrupting or disabling the data gathering unit 136, the therapy delivery unit 138, the therapy/sensing interface 140, or a combination thereof. The specific responsive action that is initiated may be selected based on which particular flag or flags are not SET. For example, in response to a first enabled flag not being SET, a first responsive action (such as, resetting a processor) may be initiated; whereas, in response to a second enabled flag not being SET, a different responsive action (such as disabling the therapy delivery unit 138) may be initiated.

In some embodiments, after the responsive action is initiated, the monitoring system may cease functioning until the monitoring system is reset (e.g., manually or responsive to an indication that the responsive action has been completed successfully). After the monitoring system is reset, the first counter may be reset, and the counter may count a subsequent monitoring period.

After reaching the second time 320, the counter may continue to count to one or more additional intermediate times, such as the nth time 330. Alternately, in some embodiments, there may be no additional intermediate times, in which case, the counter continues to count until the roll over time 340 is reached. When the nth time 330 is reached, the monitoring system may determine, at 332, whether enabled flags of the memory location are SET. A set of enabled flags at the memory location may be different at the nth time 330 than at the second time 320. For example, as described with reference to FIG. 2, an enable signal (e.g., the enable signal 210) may be provided to each memory location (e.g., dedicated register) by a corresponding software module (e.g., one of the software modules 204, 206, 208). The software modules may have different run cycles and may provide enable signals at different rates (e.g., at different intervals). Accordingly, at the second time 320 a first set of flags may be enabled, and, at the second time, a second set of flags may be enabled. The first set of flags and the second set of flags may be different (although one or more flags may be included in both the first set of flags and in the second set of flags).

When the enabled flags are SET, at 332, the monitoring system may reset the enabled flags, at 334. When one or more of the enabled flags is not SET, the monitoring system may initiate performance of an action, at 350.

After reaching the nth time 330, the counter may continue to count to one or more additional intermediate times (not shown). If there are no additional intermediate times, the counter continues to count until the roll over time 340 is reached. When the roll over time 340 is reached, the monitoring system may determine, at 342, whether enabled flags of the memory location are SET. A set of enabled flags at the memory location may be different at the roll over time 340 than at the second time 320, the nth time 330, or both. For example, at the roll over time 340 a third set of flags may be enabled. The third set of flags may be different from the first set of flags enabled at the second time 320, different from the second set of flags enabled at the nth time 330, or different from both the first set of flags and the second set of flags. However, one or more flags may be included in more than one of the first set of flags, the second set of flags, and the third set of flags. When there are more than two intermediate times, each intermediate time may be associated with an entirely distinct set of enabled flags, or may be associated with a set of flags that duplicates, overlaps, subsumes, or is subsumed by a set of enabled flags associated with another intermediate time or with the roll over time 340.

When the enabled flags are SET, at 342, the monitoring system may reset the enabled flags and reset the counter, at 344. When the counter is reset, the counter reverts to the first time 310 and again counts to the second time 320, the nth time 330 and the roll over time 340. When one or more of the enabled flags is not SET, the monitoring system may initiate performance of an action, at 350.

In FIG. 3, a first period 316 between the first time 310 and the second time 320 may have a different duration than a second period 326 between the second time 320 and the nth time 330. Also, the first period 316, the second period 320, or both, may have a different duration than a third period 336 between the nth time 330 and the roll over time 340. The duration of each period 316, 326, 336 (and possibly other periods, not shown) may be specified by parameters stored at a memory accessible to the monitoring system. For example, information describing the duration of each period 316, 326, 336 (and possibly other periods, not shown) may be stored as configuration data at one or more of the memory locations. In a particular embodiment, the monitoring system may be preconfigured (e.g., in hardware or firmware) to check enabled flags at particular durations corresponding to the duration of each period 316, 326, 336 (and possibly other periods, not shown). In this embodiment, the duration of each period 316, 326, 336 (and possibly other periods, not shown) may be predetermined based on functionality or characteristic time intervals of the monitored software modules. For example, two or more of the software modules may have a similar execution cycle. In this example, one or more of the periods 316, 326, 336 (and possibly other periods, not shown) may have a duration that corresponds to the execution cycle of the two or more software modules. In another example, when the monitoring system monitors an implantable medical device, such as the IMD 100 of FIG. 1, the duration of one or more of the periods 316, 326, 336 (and possibly other periods, not shown) may be selected based on a biological cycle (such as a heart rate, a respiratory rate, a refractory period, or another biologically related period). In yet another example, the duration of one or more of the periods 316, 326, 336 (and possibly other periods, not shown) may be selected to simplify configuration of a monitoring scheme for software monitors. To illustrate, the periods 316, 326, 336 (and possibly other periods, not shown) may have durations that are mathematically related. As a specific example, the duration of each of the periods 316, 326, 336 (and possibly other periods, not shown) may be determined based on a mathematical formula (such as geometric progression, a logarithmic progression, a linear progression, etc.).

Accordingly, the method of FIG. 3 may enable flexible and dynamic configuration of a monitoring system. For example, different monitored modules may be monitored at frequencies that closely match the execution time or frequency of each particular module. Additionally, since each monitored module may provide an enable signal to a corresponding memory location to generate an enabled flag, each module can dynamically and independently of other modules, opt into or opt out of monitoring.

Figure 4:
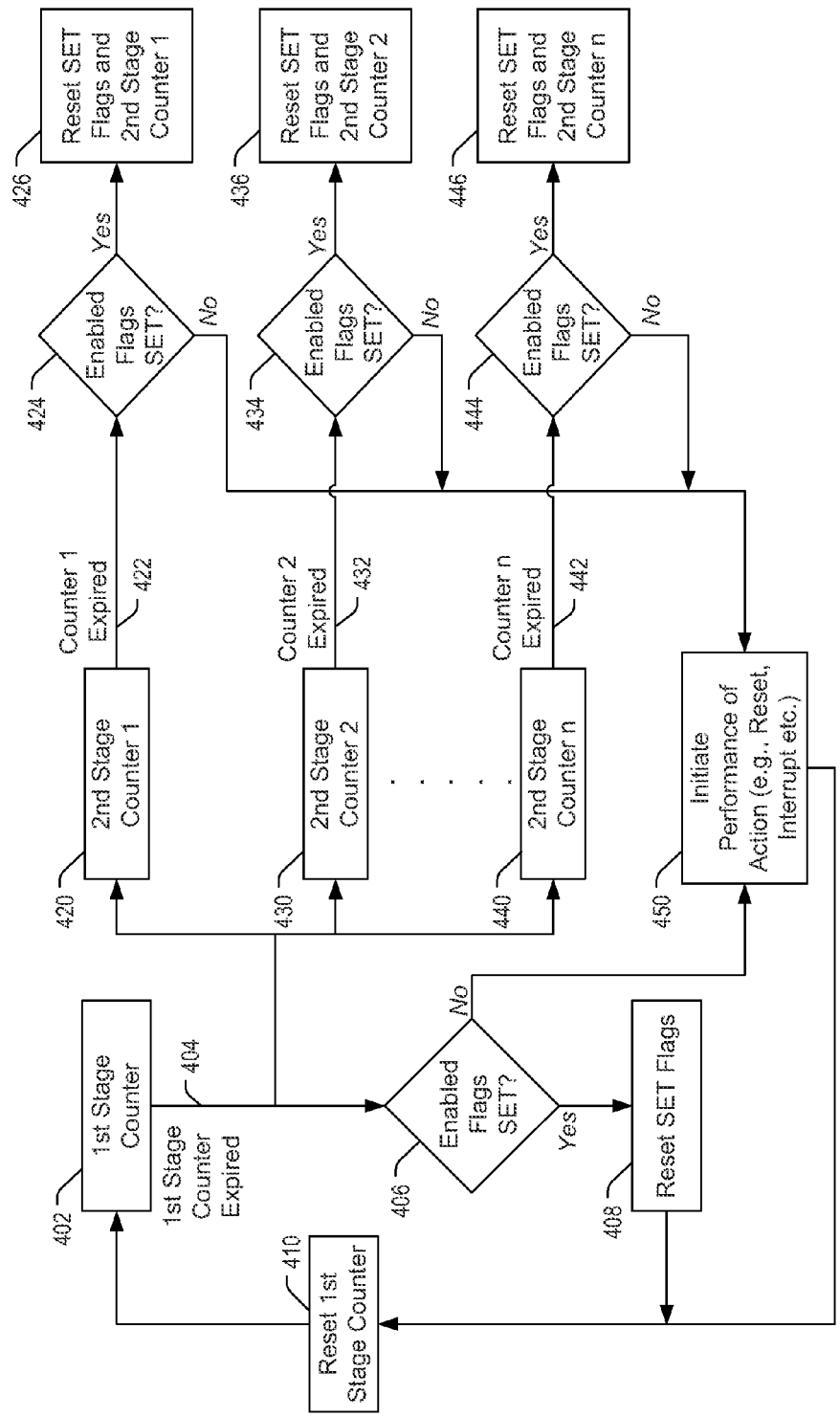
FIG. 4 is a diagram illustrating an embodiment of a method that may be implemented by a system monitor.

FIG. 4 is a diagram illustrating another embodiment of a method that may be implemented by a system monitor, such as the system monitor 120 of FIG. 1 or the monitoring system 202 of FIG. 2. In the embodiment illustrated in FIG. 4, the monitoring system may use staged counters (such as two or more of the counter 220). For example, a first stage counter 402 may count a first monitoring period and one or more second stage counters 420, 430, 440 may count one or more second monitoring periods. In the embodiment illustrated in FIG. 4, the counter stages are daisy chained. That is, the one or more second stage counters 420, 430, 440 begin counting respective monitoring periods in response to expiration of the first stage counter 402, at 404. In other embodiments, the first stage counter 402 and the one or more second stage counters 420, 430, 440 may count their respective monitoring periods independently of one another.

During operation of the monitoring system, the first stage counter 402 may count the first monitoring period (e.g., by counting from a start time to an end time). Upon expiration of the first stage counter (e.g., when the end time is reached), at 404, the one or more second stage counters 420, 430, 440 may be initiated to begin counting their respective monitoring periods. Additionally, upon expiration of the first stage counter, at 404, a determination may be made, at 406, whether enabled flags of the monitoring system are SET. If the enabled flags are all SET, the monitoring system may reset the SET flags, at 408. The monitoring system may also reset the first stage counter, at 410. If one or more of the enabled flags is not SET, the monitoring system may initiate performance of a responsive action, at 450. Examples of responsive actions may include resetting a processor or another component of a monitored device, interruption the processor or the other component of the monitored device, or disabling the processor or the other component of the monitored device. To illustrate, when the monitored device is the implantable medical device 100 of FIG. 1, the responsive action may include resetting, interrupting or disabling the data gathering unit 136, the therapy delivery unit 138, the therapy/sensing interface 140, or a combination thereof. The specific responsive action that is initiated may be selected based on which particular flag or flags are not SET. For example, in response to a first enabled flag not being SET, a first responsive action (such as, resetting a processor) may be initiated; whereas, in response to a second enabled flag not being SET, a different responsive action (such as disabling the therapy delivery unit 138) may be initiated.

In some embodiments, after the responsive action is initiated the monitoring system may cease functioning until the monitoring system is reset (e.g., manually or responsive to an indication that the responsive action has been completed successfully). After the monitoring system is reset, the first counter may be reset at 410, and the first stage counter 402 may count the first monitoring period again.

After the first stage counter expires, at 404, and the one or more second stage counters 420, 430, 440 are started, each of the one or more second stage counters 420, 430, 440 counts a respective monitoring period. For example, in the embodiment illustrated in FIG. 4, the second stage counters include a first counter 420 of the second stage, a second counter 430 of the second stage, and an nth counter 440 of the second stage. The first counter 420 may count a first monitoring period of the second stage, the second counter 430 may count a second monitoring period of the second stage, and the nth counter 440 may count an nth monitoring period of the second stage. The first, second and nth monitoring periods may have the same duration, or one or more of the first, second and nth monitoring periods may have a different duration than one or more others of the first, second and nth monitoring periods.

At expiration of each counter of the second stage counters, the monitoring system may check to see whether each enabled flag is SET. When the enabled flags are all SET, the monitoring system may reset the SET flags and the corresponding counter. When one or more of the enabled flags is not SET, the monitoring system may initiate performance of a responsive action, at 450. For example, when the first counter 420 of the second stage expires (e.g., reaches an end time of the first counter 420), at 422, the monitoring system may determine whether enabled flags are SET, at 424. When the enabled flags are all SET, at 424, the monitoring system may reset the SET flags and the first counter 420 of the second stage, at 426. When the second counter 430 of the second stage expires (e.g., reaches an end time of the second counter 430), at 432, the monitoring system may determine whether enabled flags are SET, at 434. When the enabled flags are all SET, at 434, the monitoring system may reset the SET flags and the second counter 430 of the second stage, at 436. When the nth counter 440 of the second stage expires (e.g., reaches an end time of the nth counter 440), at 442, the monitoring system may determine whether enabled flags are SET, at 444. When the enabled flags are all SET, at 444, the monitoring system may reset the SET flags and the nth counter 440 of the second stage, at 446.

In particular embodiments, particular memory locations of the monitoring system (such as the memory locations 236 of the monitoring system 202 of FIG. 2) are assigned to a respective one or more of the counter stages (e.g., the first stage counter 402 and the one or more second stage counters 420, 430, 440). For example, the enabled flags checked, at 406, when the first stage counter 402 expires may correspond to a first set of memory locations, and the enabled flags checked, at 424, when the first counter 420 of the second stage expires may correspond to a second set of memory locations. Similarly, the enabled flags checked, at 434, when the second counter 430 of the second stage expires may correspond to a third set of memory locations, and the enabled flags checked, at 444, when the nth counter 440 of the second stage expires may correspond to a fourth set of memory locations. Each of the first set of memory locations, the second set of memory locations, the third set of memory locations, and the fourth set of memory locations may be entirely distinct from one or more of the other sets of memory locations, or may overlap with, subsume, or be subsumed by one or more of the other sets of memory locations.

In a particular embodiment, software and/or hardware modules that are monitored by the monitoring system may be assigned to particular counters or counter stages based at least partially on an execution period of the software and/or hardware modules, based on an execution order of the software and/or hardware modules, or based on other factors that facilitate monitoring of the software and/or hardware modules using staged counters. For example, a particular module that executes continuously or periodically may be assigned to be monitored using the first stage counter 402. Upon expiration of the first stage counter 402, one or more diagnostic tests associated with the particular module or associated with submodules of the particular module may be executed. In this example, the second stage counters 420, 430, 440 may be used to count monitoring periods associated with the diagnostic tests.

Accordingly, the staged counters of FIG. 4 may enable flexible and dynamic configuration of the monitoring system. For example, different monitored modules may be assigned to counters that are daisy chained or independent of other counters, enabling modules to be monitored in a manner that closely matches the execution time or frequency of each particular module. Additionally, since each monitored module may provide an enable signal to a corresponding memory location to generate an enabled flag, each module can dynamically and independently of other modules, opt into or opt out of monitoring.

Figure 5:
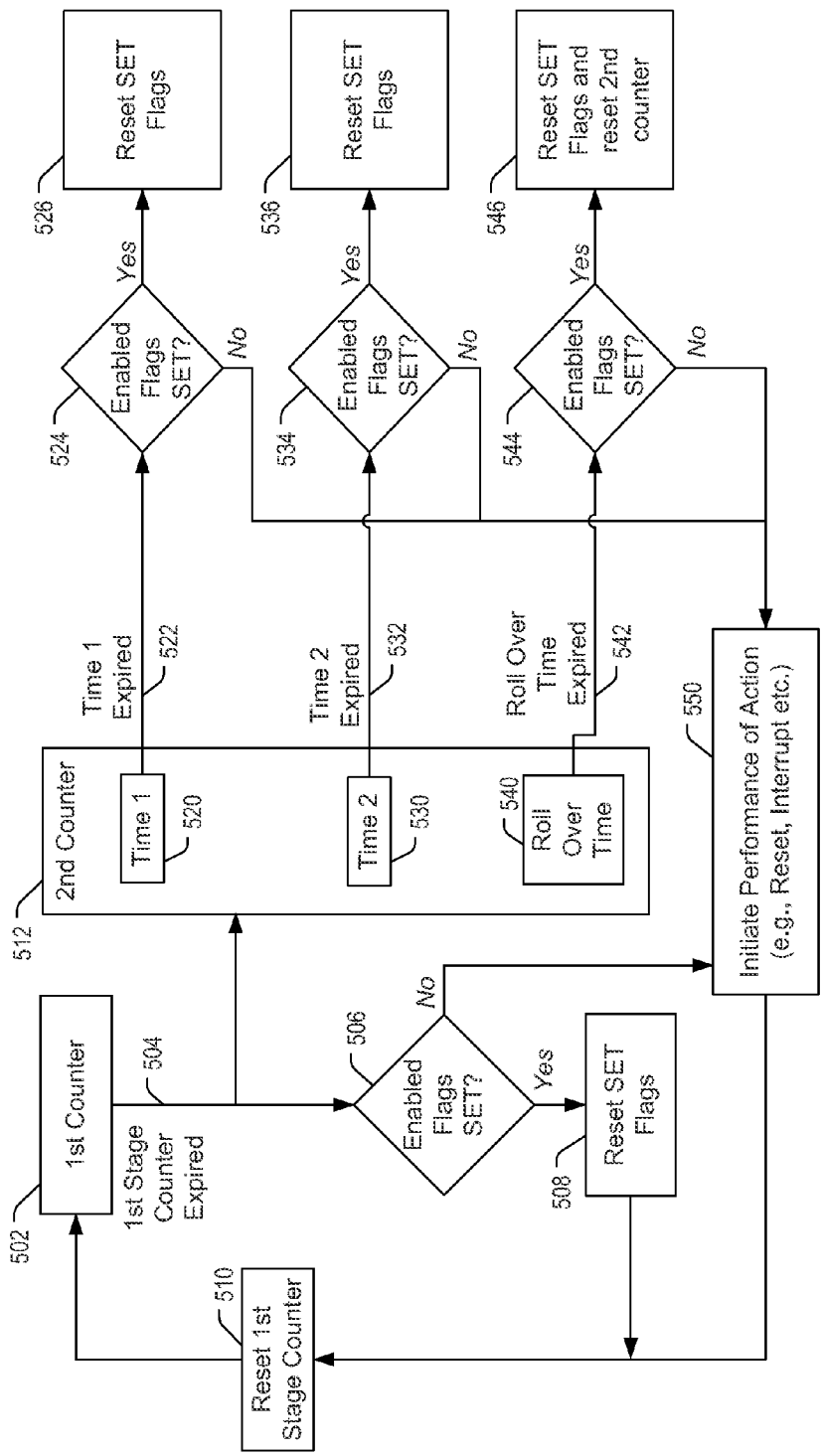
FIG. 5 is a diagram illustrating another embodiment of a method that may be implemented by a system monitor.

FIG. 5 is a diagram illustrating another embodiment of a method that may be implemented by a system monitor, such as the system monitor 120 of FIG. 1 or the monitoring system 202 of FIG. 2. The embodiment illustrated in FIG. 5, is similar to the embodiment illustrated in FIG. 4 except that in the embodiment of FIG. 5, a single second counter counts multiple monitoring periods, in a manner similar to that described with reference to FIG. 3. For example, a first counter 502 may count one or more first monitoring periods (although only one first monitoring period is illustrated in FIG. 5 to simplify the description), and a second stage counter 512 may count one or more second monitoring periods. In the embodiment illustrated in FIG. 5, the first and second counters 502, 512 are daisy chained. That is, the second stage counter 512 begins counting the one or more second monitoring periods in response to expiration of the first counter 502, at 504. In other embodiments, the first counter 502 and the second counter 512 may count their respective monitoring periods independently of one another.

During operation of the monitoring system according to the embodiment of FIG. 5, the first counter 502 may count the first monitoring period (e.g., by counting from a start time to an end time or to an intermediate time between the start time and the end time). Upon expiration of the first stage counter (e.g., when the end time or the intermediate time is reached), at 504, the second stage counter 512 may be initiated to begin counting the first time 520. Additionally, upon expiration of the first stage counter, at 504, a determination may be made, at 506, whether enabled flags of the monitoring system are SET. If the enabled flags are all SET, the monitoring system may reset the SET flags, at 508. The monitoring system may also reset the first stage counter, at 510 (if the first counter 502 has reached a roll over time). If one or more of the enabled flags is not SET, the monitoring system may initiate performance of a responsive action, at 550. Examples of responsive actions may include resetting a processor or another component of a monitored device, interruption the processor or the other component of the monitored device, or disabling the processor or the other component of the monitored device. To illustrate, when the monitored device is the IMD 100 of FIG. 1, the responsive action may include resetting, interrupting or disabling the data gathering unit 136, the therapy delivery unit 138, the therapy/sensing interface 140, or a combination thereof. The specific responsive action that is initiated may be selected based on which particular flag or flags are not SET. For example, in response to a first enabled flag not being SET, a first responsive action (such as, resetting a processor) may be initiated; whereas, in response to a second enabled flag not being SET, a different responsive action (such as disabling the therapy delivery unit 138) may be initiated.

In some embodiments, after the responsive action is initiated the monitoring system may cease functioning until the monitoring system is reset (e.g., manually or responsive to an indication that the responsive action has been completed successfully). After the monitoring system is reset, the first counter may be reset at 510, and the first counter 502 may count the first monitoring period again.

After the first stage counter expires, at 504, the second counter 512 is started. Upon expiration of the first time 520, at 522, of the second counter 512, the monitoring system may determine whether enabled flags are SET, at 524. When the enabled flags are all SET, at 524, the monitoring system may reset the SET flags, at 526. When one or more of the enabled flags is not SET, the monitoring system may initiate performance of a responsive action, at 550. When the second time 530 of the second counter 512 expires, at 532, the monitoring system may determine whether enabled flags are SET, at 534. When the enabled flags are all SET, at 534, the monitoring system may reset the SET flags, at 536. When one or more of the enabled flags is not SET, the monitoring system may initiate performance of a responsive action, at 550. When the roll over time 540 of the second counter 512 expires, at 542, the monitoring system may determine whether enabled flags are SET, at 544. When the enabled flags are all SET, at 544, the monitoring system may reset the SET flags and may reset the second counter 512, at 546. When one or more of the enabled flags is not SET, the monitoring system may initiate performance of a responsive action, at 550.

In particular embodiments, particular memory locations of the monitoring system (such as the memory locations 236 of the monitoring system 202 of FIG. 2) are assigned to the first counter 502, the second counter 512, or both. For example, the enabled flags checked, at 506, when the first counter 502 expires may correspond to a first set of memory locations, and the enabled flags checked, at each of 524, 534 and 544, when the times 520, 530, 540 of the second counter 512 expire may correspond to a second set of memory locations. The first set of memory locations and the second set of memory locations may be entirely distinct from one another, may partially overlap one another, or one of the sets of memory locations may subsume the other set of memory locations.

Accordingly, the counters 502, 512 of FIG. 5 may enable flexible and dynamic configuration of the monitoring system. For example, different monitored modules may be assigned to counters that are daisy chained or independent of other counters, enabling modules to be monitored in a manner that closely matches the execution time or frequency of each particular module. Additionally, since each monitored module may provide an enable signal to a corresponding memory location to generate an enabled flag, each module can dynamically and independently of other modules, opt into or opt out of monitoring.

Figure 6:
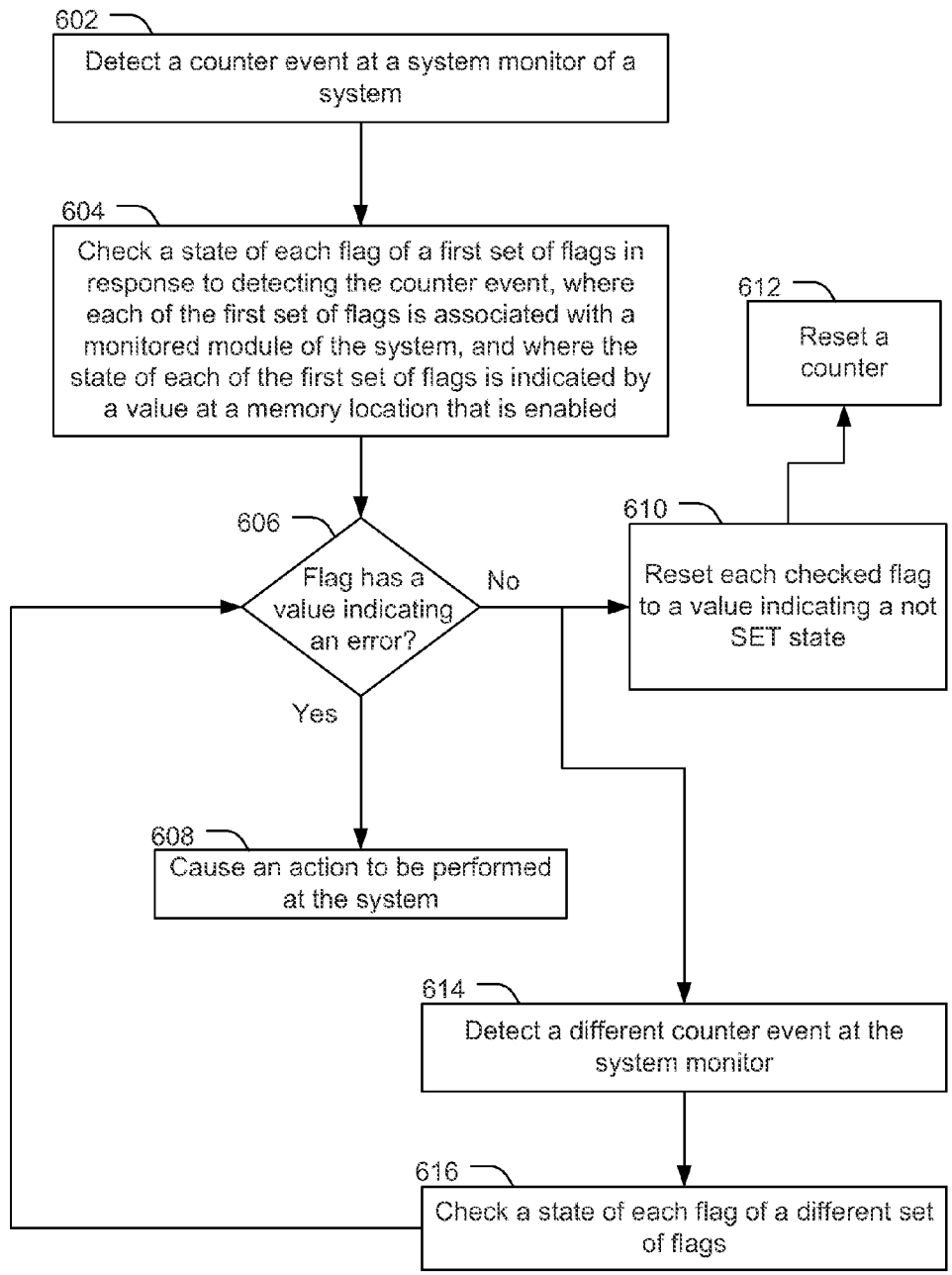
FIG. 6 is a flow chart of a particular embodiment of method of monitoring a system.

FIG. 6 is a flow chart of a particular embodiment of a method of monitoring a system. The method of FIG. 6 may be performed by a system monitor or monitoring system, such as the system monitor 120 of FIG. 1 or the monitoring system 202 of FIG. 2.

The method includes, at 602, detecting a counter event at a system monitor of a system. The counter event may be detected when a counter of the system monitor reaches an end value or an intermediate value between a starting value and the end value. For example, the counter event may be detected when the counter 220 of FIG. 2 reaches the end value. In another example, the counter event may be detected when the counter reaches one of the second time 320, the nth time 330 or the roll over time 340 of FIG. 3.

The method also includes, at 604, in response to detecting the counter event, checking a state of each flag of a first set of flags. In a particular embodiment, each of the first set of flags is associated with a monitored module of the system, and the state of each of the first set of flags is indicated by a value at a memory location that is enabled. For example, the first set of flags may correspond to the enabled flags 226 of FIG. 2, each of which is associated with one of the software modules 204, 206, 208 monitored by the monitoring system. In this example, one or more other memory locations may not be enabled. The memory locations that are not enabled may not be checked or no action may be taken if a flag is not SET at a memory location that is not enabled.

The method may also include, at 606, determining whether one or more of the flags has a value indicating an error associated with a monitored module. In response to determining that at least one flag has a value indicating an error associated with the monitored module, the method includes, at 608, causing an action to be performed at the system. The action may include, for example, resetting a processor or another component of the system, interruption the processor or the other component of the system, or disabling the processor or the other component of the system. To illustrate, when the system corresponds to the IMD 100 of FIG. 1, the responsive action may include resetting, interrupting or disabling the data gathering unit 136, the therapy delivery unit 138, the therapy/sensing interface 140, or a combination thereof. The specific action that is initiated may be selected based on which particular flag or flags are not SET. In response to determining that each checked flag (e.g., each enabled flag of the first set of flags) has a value indicating no error associated with the monitored module (e.g., a SET value), the method includes, at 610, resetting each checked flag to a value indicating a not SET state.

The method may also include, at 612, resetting a counter depending on the counter event that was detected. For example, when the detected counter event was a counter reaching a roll over time, the counter that reached the roll over time may be reset.

In a particular embodiment, the method also includes, at 614, detecting a different counter event at the system monitor. For example, a subsequent counter event (e.g., a second counter event) may be detected after the counter event (e.g., a first counter event) is detected. The second counter event may indicate that the counter has reached a subsequent counter value, such as a subsequent intermediate time or a roll over time. Alternately, the first counter event may be associated with a first counter expiring (e.g., reaching an end time) and the second counter event may be associated with a second counter expiring (e.g., reaching an end time) or reaching an intermediate time (such as the first time 520 of FIG. 5).

In this embodiment, the method may also include, at 616, checking a state of each flag of a different set of flags (e.g., a second set of flags). The second set of flags may include flags that are enabled when the second counter event is detected. The method may continue, at 606, to determine whether a flag (e.g., a flag of the second set of flags) has a value indicating an error. When a flag has a value indicating an error, the method may include, at 608 causing an action to be performed at the system. When no checked flag (e.g., no enabled flag) has a value indicating an error, the method may include, at 610 resetting the checked flags. Additionally, the method may include detecting one or more additional counter events, at 614.

Accordingly, the method of FIG. 6 may enable operation of a flexible and dynamically configurable monitoring system. For example, different monitored modules may be assigned to counters that are daisy chained or independent of other counters, enabling modules to be monitored in a manner that closely matches the execution time or frequency of each particular module. Additionally, since each monitored module may provide an enable signal to a corresponding memory location to generate an enabled flag, each module can dynamically and independently of other modules, opt into or opt out of monitoring.

Those of skill in this art and who also have the benefit of this disclosure may appreciate that the various illustrative logical blocks, configurations, modules, circuits, and algorithm steps described in connection with the embodiments disclosed herein may be implemented as electronic hardware, computer software, or combinations of both. Various illustrative components, blocks, configurations, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The methods, processes, or algorithms described in connection with the embodiments disclosed herein may be embodied directly in hardware, in a software module executed by a processor, or in a combination of the two. A software module may reside in random access memory (RAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of storage medium usable to store potentially executable code. Included is a non-transitory (e.g. tangible) storage medium coupled to the processor or other logic able to execute instructions such that the data, including any instructions, can be read and, where needed, written, to the storage medium. In the alternative, the storage medium may be integral to the processor. The processor and the storage medium may reside in an application-specific integrated circuit (ASIC). The ASIC may reside in a computing device, and, there may be a plurality of such ASICs or processors or microprocessors in any particular device, or in a user terminal. In the alternative, the processor and the storage medium may reside as discrete components in a computing device or user terminal.

Various embodiments have been shown and described, and are intended to be examples of the system monitor disclosed herein. The system monitor is not limited to these specifics, and will be understood to include all modifications, variations, and implementations as would be apparent to one skilled in the art who also has the benefit of this disclosure. For example, equivalent elements may be substituted for those specifically shown and described, certain features may be used independently of other features, and the number and configuration of various vehicle components described above may be altered, all without departing from the scope of the disclosed system monitor as claimed.

The phraseology and terminology employed herein is for the purpose of description and not of limitation. Accordingly, the foregoing description of various embodiments of the system monitor, as set forth above, are intended to be illustrative, not limiting. Various changes, modifications, and/or adaptations may be made without departing from the scope of this disclosure and its claims.

What is claimed is:

1. A method comprising:
during a first monitoring period, receiving enable signals from monitored modules of a system, wherein each monitored module provides at least one enable signal to enable at least one memory location associated with the monitored module;
establishing enabled memory locations in response to the enable signals;
during the first monitoring period, receiving one or more set signals from one or more of the monitored modules;
responsive to each set signal, setting a value at an enabled memory location that is associated with the monitored module that sent the set signal;
detecting a counter event indicating an end of the first monitoring period;
based on detecting the counter event, checking a value stored at each enabled memory location; and in response to determining that at least one enabled memory location stores a value indicating an error associated with a particular monitored module, causing an action to be performed at the system.

2. The method of claim 1, wherein the enabled memory locations are dedicated registers.

3. The method of claim 1, wherein the action comprises disabling therapy provided by the system, and further comprising subsequently enabling the therapy based on an input received from an external device.

4. The method of claim 1, wherein the system includes or is included within an implantable medical device.

5. The method of claim 4, wherein the action comprises disabling therapy provided by the implantable medical device.

6. The method of claim 1, further comprising decrementing a count value of a counter from a starting value to an ending value, wherein the counter event is detected in response to the count value reaching the ending value.

7. The method of claim 6, further comprising:
resetting each enabled memory location to a particular value indicating a not-SET state after checking the value stored at each enabled memory location; and
resetting the counter to the starting value.

8. The method of claim 1, further comprising decrementing a count value from a starting value to an ending value, wherein the counter event is detected in response to the count value reaching a predetermined value that is between the starting value and the ending value.

9. The method of claim 1, wherein the action comprises sending a reset signal to the particular module, setting an interrupt on at least one module, or both.

10. The method of claim 1, further comprising:
decrementing a first counter from a first starting value to a first ending value, wherein the counter event is detected in response to the first counter reaching a first particular value, and further comprising:
decrementing a second counter from a second starting value to a second ending value;
detecting a second counter event in response to the second counter reaching a second particular value; and
in response to detecting the second counter event, checking values stored at second enabled memory locations, wherein the enabled memory locations are distinct from the second enabled memory locations.

11. The method of claim 10, wherein the second counter is initiated in response to detecting the counter event.

12. The method of claim 10, wherein the first starting value is different from the second starting value.

13. The method of claim 10, wherein the first counter and the second counter operate concurrently.

14. A non-transitory computer-readable storage medium storing instructions executable by a processor to cause the processor to perform operations comprising:
during a first monitoring period, receiving enable signals from monitored modules of a system, wherein each monitored module provides at least one enable signal to enable at least one memory location associated with the monitored module;
establishing enabled memory locations in response to the enable signals;
during the first monitoring period, receiving one or more set signals from one or more of the monitored modules;
responsive to each set signal, setting a value at an enabled memory location that is associated with the monitored module that sent the set signal;
detecting a counter event indicating an end of the first monitoring period;
based on detecting the counter event, checking a value stored at each enabled memory location; and
in response to determining that at least one enabled memory location stores a value indicating an error associated with a particular monitored module, causing an action to be performed at the system.

15. The non-transitory computer-readable medium of claim 14, wherein the operations further comprise reversing the action in response to receipt of a particular signal from a device external to the system.

16. The non-transitory computer-readable medium of claim 14, wherein the system includes or is included within an implantable medical device, and wherein the action comprises disabling therapy provided to a patient via the implantable medical device.

17. A system comprising:
circuitry configured to receive enable signals from monitored modules during a first monitoring period and configured to establish enabled memory locations in response to the enable signals, wherein each monitored module provides at least one enable signal to enable at least one memory location associated with the monitored module;
circuitry configured to receive one or more set signals from one or more of the monitored modules during the first monitoring period and configured to, responsive to each set signal, set a value at an enabled memory location that is associated with the monitored module that sent the set signal;
circuitry configured to detect a counter event indicating an end of the first monitoring period;
circuitry configured to, based on detection of the counter event, check a value stored at each enabled memory location; and
circuitry configured to, in response to a determination that at least one enabled memory location stores a value indicating an error associated with a particular monitored module, cause an action to be performed.

18. The system of claim 17, wherein at least one enabled memory location is a dedicated register.

19. The system of claim 17, wherein the system includes or is included within an implantable medical device and the action comprises disabling therapy provided to a patient via the implantable medical device.

20. The system of claim 19, wherein the therapy is provided by a module that is distinct from the particular monitored module associated with the error.

* * * * *